United States Patent
Rose

[11] 3,985,125
[45] Oct. 12, 1976

[54] VAGINAL SPECULUM

[76] Inventor: Ewald Rose, August-Antz-Str. 25, 55 Trier-Ehrang, Germany

[22] Filed: Mar. 21, 1975

[21] Appl. No.: 560,640

[30] Foreign Application Priority Data
Mar. 26, 1974 Germany............................. 2414369

[52] U.S. Cl. ............................................... 128/17
[51] Int. Cl.² .......................................... A61B 1/32
[58] Field of Search ............... 128/3, 17, 18, 19, 20; 129/17

[56] References Cited
UNITED STATES PATENTS
3,890,961  6/1975  Moore et al. ......................... 128/17

Primary Examiner—Robert W. Michell
Assistant Examiner—Henry S. Layton
Attorney, Agent, or Firm—Robert W. Beach; R. M. Van Winkle

[57] ABSTRACT

In a vaginal speculum comprising two members each having a main limb, the main limbs can be inserted into a vagina whilst lying while and moved to pivot and move apart to maintain the vagina open for examination or treatment. One of the members has cheeks from which extend pins which engage slots in walls of a yoke of the other member; and each cheek has a toothed strip, a tooth on the adjacent wall of the yoke co-operating therewith to lock the speculum open. The yoke is resilient so that by deformation thereof the teeth can be caused to disengage the strips to allow closure of the speculum.

7 Claims, 5 Drawing Figures

VAGINAL SPECULUM

FIELD OF THE INVENTION

This invention relates to a vaginal speculum for keeping the vagina open during medical examination.

Various types of vaginal mirrors or vagina specula are known which are used for medical examination of women. These known devices are usually made of metal and have two expanding parts which are mutually sluable between a closed condition, in order to enable them to be inserted into the vagina, and an expanded condition, to dilate the vagina and maintain the dilation. The known devices have, furthermore, a locking mechanism in order to maintain the vaginal speculum in the expanded position during examination.

In addition, devices of the said type are also known which are of plastics material and are intended to be disposable, such as disclosed in U.S. Pat. No. 3,890,961.

Known devices have the disadvantage either that the speculum can be locked and released only by using both hands, or that the locking device is in the form of a toothed rod which projects from the device in such a way that it either hinders the field of manipulation of the doctor, who has to work through the opened speculum, or that it comes into contact with the patient during examination.

OBJECT OF THE INVENTION

An object of the invention is to provide a vaginal speculum which can be manipulated with one hand and which allows a doctor using the device to have a good field to work in.

BRIEF STATEMENT OF THE INVENTION

The invention provides a vaginal speculum, for keeping the vagina dilated during medical examination. Such speculum includes a first member having an elongated limb, one end of which is insertable into a vagina and the other end of which carries a pair of spaced lateral cheeks each having two pins projecting outward therefrom and a handle extending at an angle to a main limb of the member and a second member also having a main elongated limb disposable alongside the limb of the first member. At one end of the latter limb is a yoke having sidewalls disposable substantially parallel to the cheeks of the first member, each sidewall including slots for reception of the pins of the adjacent cheek and an actuating lever extending at an angle to the main limb for effecting expansion of the speculum. The outer side of each cheek of the first member is a toothed strip projecting outwardly therefrom toward the adjacent yoke sidewall of the second member. On the oppositely lying inner side of the respective yoke sidewall is a tooth cooperating with the toothed strip. The yoke is resilient so that said teeth can be brought out of engagement with said toothed strips by deformation of said yoke.

Advantageously arranged at the rear end of each cheek of the first member is a laterally projecting rib, the height of which rib is approximately equal to the height of the toothed strip. The rib forms a fulcrum about which the yoke sidewalls deform.

In accordance with a further development, the toothed strip is curved with the center of curvature on the side of the strip remote from the main limb and the two cheeks of the first member are connected by a stiffening plate.

Advantageously projecting from the rear of each yoke sidewall in line with the yoke tooth is an ear to facilitate deformation of the yoke and release of its teeth from the tooth strips. Furthermore, the slotted openings are preferably arcuate, having different centers of curvature, both centers being located at the sides of their respective slots remote from the main limb.

DESCRIPTION OF A PREFERRED EMBODIMENT

Figure 1:
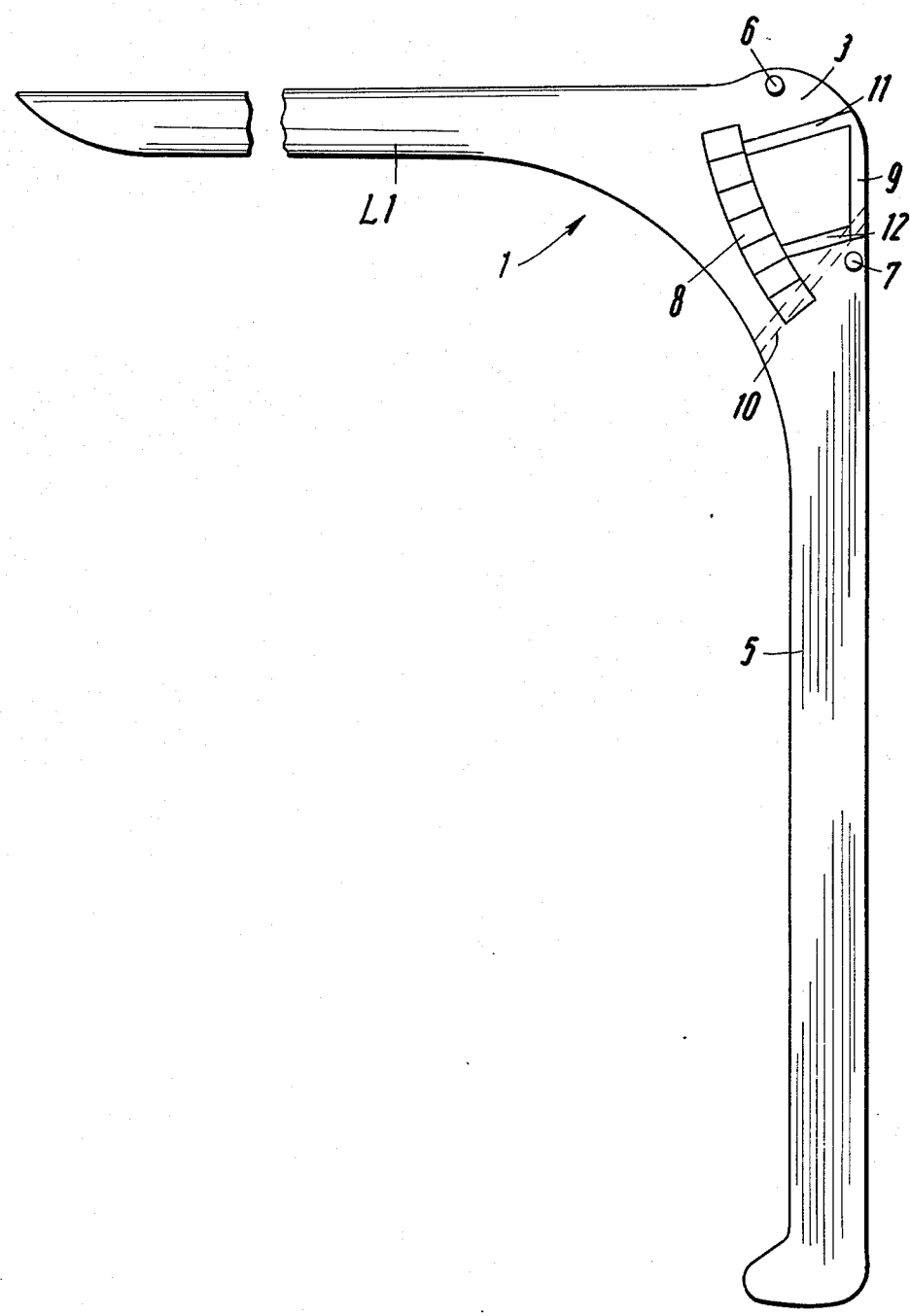
FIG. 1 is a side elevation of a first member of a preferred embodiment of vaginal speculum of the invention.

A preferred embodiment of vaginal speculum conforming to the invention consists of a first member 1 and a second member 2 which members are advantageously made of plastic material.

The first member 1, which has a smooth channel-shaped main limb L1 insertable into a vagina with the concave side of the channel uppermost, has at its rear wider end lateral cheeks 3 and 4 which fair into a handle 5 disposed at a right angle to the main limb. Each of the cheeks 3 and 4 carries on its outer side two pins 6 and 7 which project transversely to the plane of expansion of the speculum. Each cheek also carries a toothed strip 8 which is curved, the center of curvature being on the side of the strip remote from limb L1, the teeth of which project outwardly from the cheek. Pins 6 and 7 are rearward of the toothed strip and are spaced apart along a line generally parallel to a line connecting the ends of the toothed strip 8. Provided at the rear edge of each of the cheeks 3 and 4 is a short rib 9 which extends in the direction of the handle 5 and the outer edge of which is designed as a fulcrum as hereinafter described. The inner sides of the two cheeks 3 and 4 are tied together by a stiffening plate 10, which plate also serves as a fluid collecting plate. In addition, outer stiffening ribs 11 and 12 spanning from toothed strip 8 to fulcrum rib are provided. The surface of the inner side of the first member especially its channel-shaped main limb, is matt in order to avoid light reflection during examination.

Figure 2:
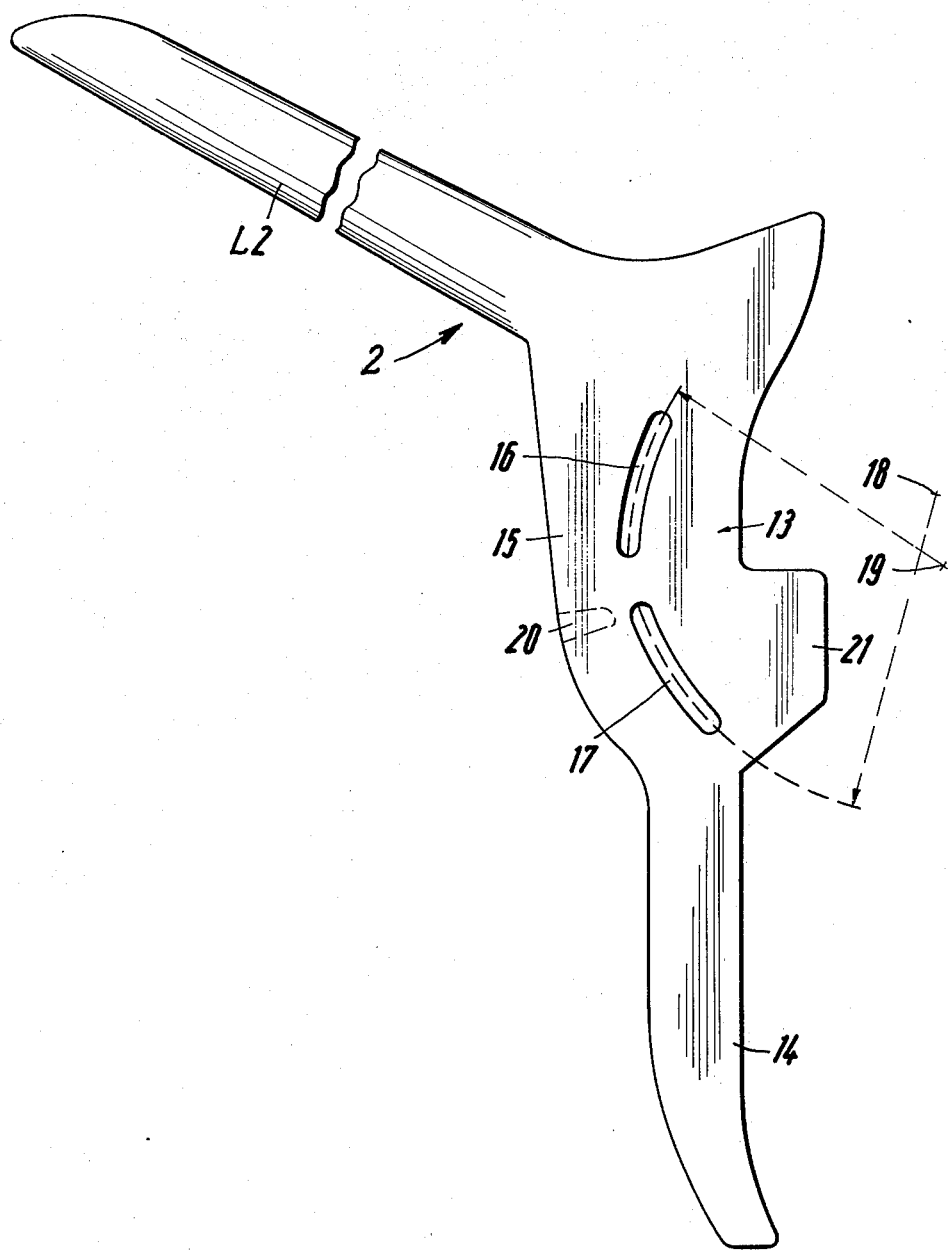
FIG. 2 is a corresponding side elevation of a second member thereof.

The main limb L2 of second member 2 is of smooth channel shape, underlies the first member main limb L1, is curved upward oppositely to the first member 1 and its surface is matt. It has at its rear end a yoke 13 which extends at an angle of approximately 120° to the main limb. The free end portion 14 of the yoke 13 is an actuating lever for effecting expanding movement. Provided in the sidewalls 15 of the yoke 13 are two slots 16 and 17 which are arcuate sections of circles having different centers 18 and 19 which centers are located at the sides of their respective slots opposite the yoke side from which main limb L2 projects (as can be seen in FIG. 2). Projecting from the inner side of each yoke sidewall is a tooth 20 which co-operates with the corresponding toothed strip 8 of the first member 1. Provided at the rear edge of each yoke sidewall, in line with the tooth 20, is an ear 21. When such ears are squeezed toward each other, the yoke sidewalls tilt about ribs 9 on the cheeks 3 and 4 to spread the forward edge margins of the sidewalls, thereby separating teeth 20 from toothed strip 8 sufficiently to permit normal contracting vaginal force to press the main limbs L1 and L2 together.

Figure 3:
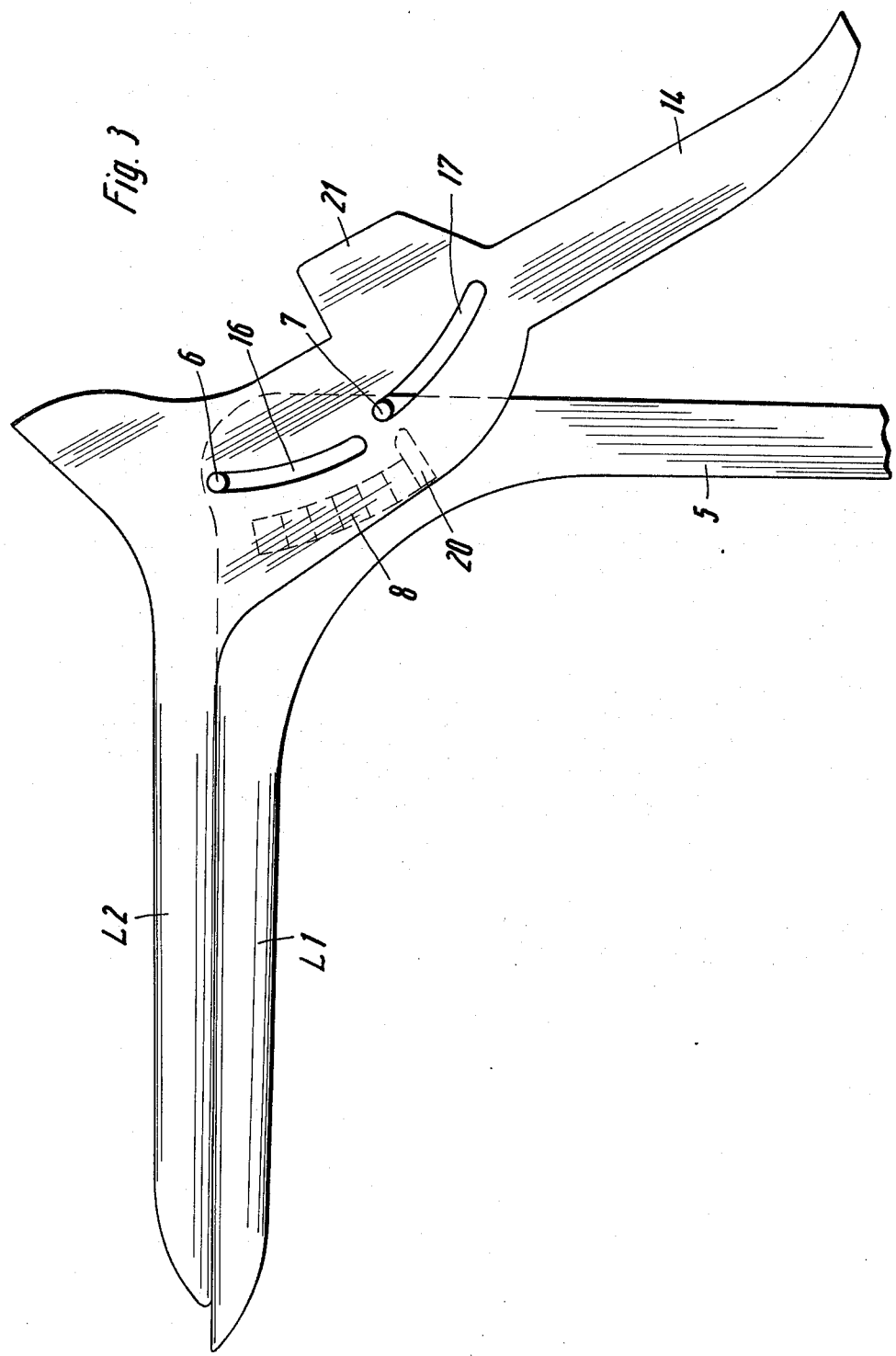
FIG. 3 is a side elevation of the speculum in closed condition.
Figure 4:
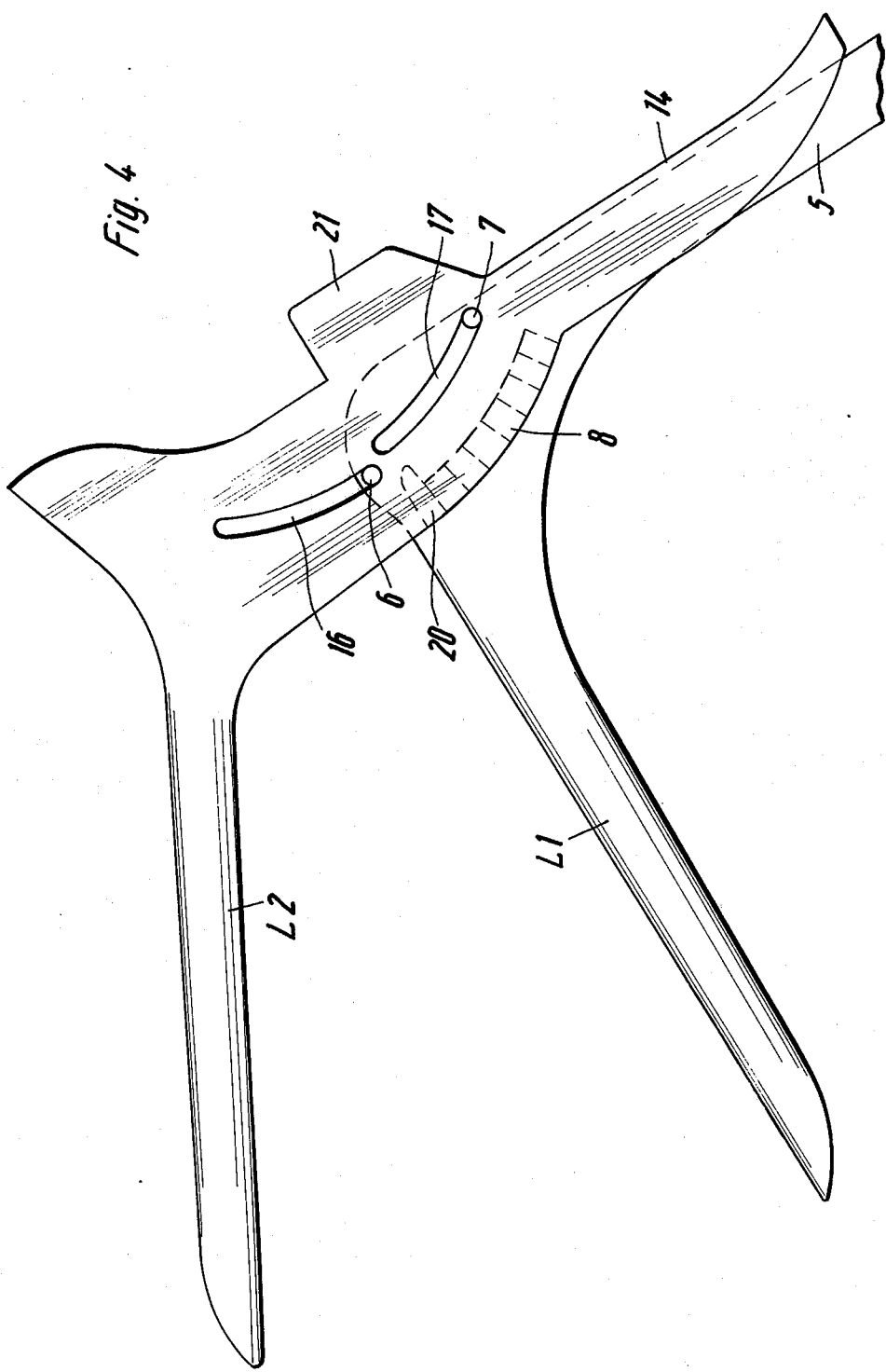
FIG. 4 is a side elevation of the speculum in an expanded condition.
Figure 5:
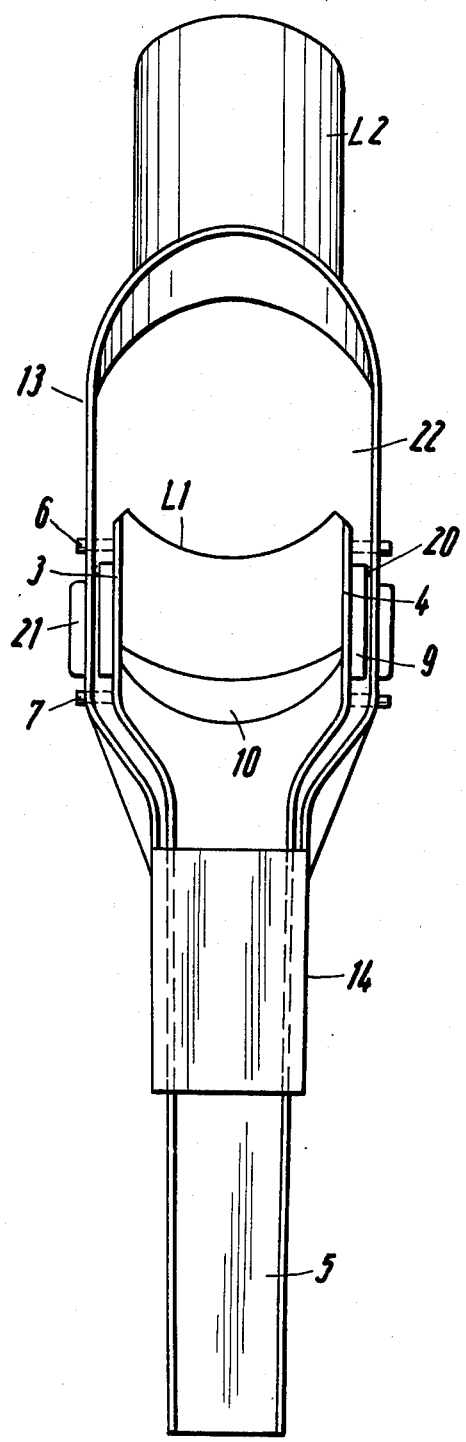
FIG. 5 is a rear elevation of the speculum in the expanded condition of FIG. 4.

The speculum of the invention is inserted in a closed condition (FIG. 3) into the vagina, during which insertion the doctor holds the device by the handle 5 with one hand. Pressure exerted by the thumb or the heel of the thumb on the actuating lever 14 effects expansion of the device during which, as a result of the arrangement of the pins 6, 7 and the slots 16, 17, the second member 2 swivels relative to the first member 1. At the same time, limb L2 is displaced from limb L1 (FIG. 4), so that the opening 22 (FIG. 5) formed between the members enlarges with increasing expansion. By this means a large area of manipulation is afforded to the doctor, whether for observation or for surgical operation. The plate 10, which serves for reinforcement, between the cheeks of the first member 1 serves, during the treatment, simultaneously for the collecting of cut-out parts of tissue or blood and as support for an examination instrument which can be inserted through the speculum.

When the speculum is to be closed again, then, using the thumb and forefinger of the same hand which holds the speculum, the two actuating ears 21 are squeezed toward each other which, as a result of the elasticity of the yoke 13, causes the yoke to tilt about the tilting edges of the ribs 9 of the first member 1 serving as fulcrums. Consequently, the inner edge margins of sidewalls 14 and 15 are spread so that the teeth 20 on the inner side of the yoke are released from engagement with the respective toothed strips 8 of the first member. As soon as the teeth are free, the speculum closes through pressure of the vagina on limbs L1 and L2. The closed speculum can then in turn be removed from the vagina.

I claim:

1. A vaginal speculum including a first member having a limb insertable into a vagina, a handle extending transversely of the limb, a pair of spaced substantially parallel cheeks connecting the rearward end of the limb and the handle, a second member having a limb insertable into a vagina and a yoke carried by the rearward end of such limb including spaced substantially parallel sheet sidewalls embracing the first member cheeks, guide means interconnecting and guiding the first and second members for relative swinging and spreading movement of the respective limbs, the cheeks and yoke sidewalls being disposed substantially parallel to the plane of movement of the limbs, and interlocking teeth means for locking the first and second members with their respective limbs in selected swung and spread relationship, the improvement comprising the interlocking teeth means including a row of teeth carried by each of the cheek means and the teeth of said row projecting outward generally transversely of the limb, a tooth carried by and projecting inward from each yoke sidewall and engageable with the adjacent row of teeth, the yoke sidewalls being flexible, and means for flexibly tilting the yoke sidewalls and thereby disengaging the engaged teeth.

2. The vaginal speculum defined in claim 1, in which the yoke-tilting means includes a rib carried by each cheek engageable with the adjacent flexible sidewall between the interlocking teeth means and the tilting means and forming a fulcrum for tilting of the sidewall to disengage the engaged teeth.

3. The vaginal speculum defined in claim 2, in which the yoke-tilting means includes ears projecting from the edges of the sidewalls directly rearwardly of the teeth carried by such sidewalls.

4. The vaginal speculum defined in claim 1, in which each row of teeth is arcuate, the center of curvature being at the side of such row remote from the first member limb.

5. The vaginal speculum defined in claim 1, and a stiffening and collecting plate connecting the cheeks of the first member.

6. The vaginal speculum defined in claim 1, in which the guide means include a pair of arcuate slots in each yoke sidewall having different centers of curvature at the side of said slots remote from the limbs, and a pair of pins projecting from each cheek through the corresponding slots of the adjacent sidewalls.

7. A vaginal speculum including a first member having a limb insertable into a vagina, a handle extending transversely of the limb, a pair of spaced substantially parallel cheeks connecting the rearward end of the limb and the handle, a second member having a limb insertable into a vagina and a yoke carried by the rearward end of such limb including spaced substantially parallel sheet sidewalls embracing the first member cheeks, guide means interconnecting and guiding the first and second members for relative swinging and spreading movement of the respective limbs, the cheeks and yoke sidewalls being disposed substantially parallel to the plane of movement of the limbs, and interlocking teeth means for locking the first and second members with their respective limbs in selected swung and spread relationship, the improvement comprising the guide means including a pair of arcuate slots in each yoke sidewall having their centers of curvature at the side of said slots remote from the limbs, and a pair of pins projecting from each cheek through the corresponding slots of the adjacent sidewalls.

* * * * *

PO-1050
(5/69)

UNITED STATES PATENT OFFICE
CERTIFICATE OF CORRECTION

Patent No. 3,985,125            Dated October 12, 1976

Inventor(s) Ewald Rose

It is certified that error appears in the above-identified patent and that said Letters Patent are hereby corrected as shown below:

Title page, section 57 (Abstract), line 3, cancel "while" and insert --parallel--.

Signed and Sealed this

Twenty-second Day of March 1977

[SEAL]

Attest:

RUTH C. MASON
*Attesting Officer*

C. MARSHALL DANN
*Commissioner of Patents and Trademarks*